United States Patent [19]

Barsomian et al.

[11] Patent Number: 5,238,821
[45] Date of Patent: Aug. 24, 1993

[54] ENDO F-FREE PNGASE

[75] Inventors: Gary D. Barsomian, Georgetown; James R. Rasmussen, Boston; Tracy L. Johnnson, Belmont, all of Mass.

[73] Assignee: Genzyme Corporation, Cambridge, Mass.

[21] Appl. No.: 798,270

[22] Filed: Nov. 20, 1991

Related U.S. Application Data

[63] Continuation of Ser. No. 353,139, May 16, 1989, abandoned.

[51] Int. Cl.$^5$ .................. C12P 21/06; C12N 9/24; C12N 15/56; C12N 15/63
[52] U.S. Cl. ..................... 435/69.1; 435/200; 435/172.3; 435/252.33; 435/320.1; 435/227; 536/23.2; 536/23.7; 536/24.32; 930/200; 930/240; 935/14; 935/73
[58] Field of Search ............ 435/69.1, 172.3, 228, 435/252.33, 252.31, 252.35, 320.1, 200, 227; 536/27

[56] References Cited

U.S. PATENT DOCUMENTS 4,999,294  3/1991  Looney et al. ................. 435/199

OTHER PUBLICATIONS

Kohno et al., *Biochim. et Biophys. ACTA* 258: 600–617, 1972.
Takahashi et al, *J. Biochem 84:* 1467–1473, 1978.
*Enzyme Nomenclature*, 1972 edition, pp. 256–257, 352–353.
*Enzyme Nomenclature*, 1984 edition, pp. 4–5, 366–375, 524–525, 560–561.
Taga, E. M. et al., "Structural and Chemical Characterization of a Homogeneous Peptide N–Glycosidase from Almond", *Biochemistry*, vol. 23, No. 5, pp. 815–822, 1984.
Langer, B. G. et al., "Deglycosylation of a Native Protease-Sensitive Glycoprotein by Peptide N–Glycosidase F without Protease Inhibitors", *Analytical Biochemistry*, 166, pp. 212–217 (1987).
Tarentino et al., J. Biol. Chem. 257:10776 (1982).
Plummer et al., J. Biol. Chem. 259:10700 (1984).
Tarentino et al., Biochem. 24:4665 (1985).
Hirani et al., Analytical Biochemistry 162:485 (1987).
Plummer et al., Eur. J. Biochem. 163:167 (1987).
Tarentino et al., Methods in Enzymology 138:770 (1987).

*Primary Examiner*—Robert A. Wax
*Assistant Examiner*—Stephen Walsh
*Attorney, Agent, or Firm*—Fish & Richardson

[57] ABSTRACT

An enzyme sample having Peptide-N$^4$-(N-acetyl-$\beta$-N-glucosaminyl) asparagine Aminidase F (PNGase F) activity completely free from Endo-$\beta$-N-acetylglucosaminidase F (Endo F) activity.

10 Claims, 2 Drawing Sheets

ENDO F-FREE PNGASE

This is a continuation of copending application(s) Ser. No. 07/353,139 field ON may 16, 1989 now abandoned.

BACKGROUND OF THE INVENTION

This invention relates to the enzyme Peptide-$N^4$-(N acetyl-$\beta$-N-glucosaminyl) asparagine aminidase (hereinafter, PNGase).

Tarentino et al. 257 J. Biol. Chem. 10776, 1982 describe a peptide: N-glycosidase isolated from almond emulsion (hereinafter PNGase A). They state that this enzyme has potential for use in structural analysis of glycopeptides.

Plummer et al. 259 J. Biol. Chem. 10700, 1984 state that Endo-$\beta$-N-acetylglucosaminidase F (hereinafter, Endo F) preparations from *Flavobacterium meningosepticum* also contain a peptide N-glycosidase activity (PNGase F). This PNGase activity cleaves the $\beta$-aspartylglycosylamine linkage of N linked carbohydrate chains from glycoproteins, releasing a full length, or intact, oligosaccharide. All the Endo F preparations were mixtures of Endo F and PNGase F activities. Partial separation of the two enzyme activities was achieved by differential ammonium sulfate precipitation, and column chromatography.

Tarentino et al. 24 Biochem. 4665, 1985 describe separation of Endo F and PNGase F by ammonium sulfate precipitation and gel filtration on TSK HW-55(S). The PNGase F activity obtained is stated to be nearly free of Endo F (containing 0.4% Endo F activity). The authors state that deglycosylation of native proteins by PNGase F can provide a useful approach for investigating structure function studies of biologically active glycoproteins.

Hirani et al. 162 Analytical Biochemistry 485, 1987 describe use of PNGase F to release asparagine-linked oligosaccharides for structural analysis. They state that the structure of the released oligosaccharides can be analyzed by HPLC.

Plummer et al. 163 Eur. J. Biochem. 167, 1987 describe PNGase activities in lentil, split pea, pinto bean, lima bean, barley, and raw wheat germ.

Tarentino et al., 138 Methods in Enzymology 770, 1987 describe a standard protocol for isolation of PNGase F activity, and an assay for that enzyme activity.

Referring to FIG. 1, the different activities of PNGase and Endoglycosidase F (Endo F) on glycoproteins and glycopeptides are shown. A PNGase cleaves the bond between an N acetylglucosamine residue and an asparagine residue, while Endo F cleaves the bond between two adjacent N acetylglucosamine residues. Thus, PNGase provides a full length carbohydrate chain, while Endo F provides a shortened chain.

SUMMARY OF THE INVENTION

In a first aspect, the invention features an enzyme sample which has PNGase F activity and which is completely free of Endo F activity.

By PNGase activity is meant an enzyme which cleaves carbohydrate moieties from asparagine residues of glycoproteins or glycopeptides at a position adjacent to the asparagine residue, i.e., an enzyme exhibiting peptide-$N^4$-(N-acetyl$\beta$-N-glucosaminyl) asparagine aminidase activity. By PNGase F is meant a PNGase isolated from a Flavobacterium species. The action of a PNGase releases full-length oligosaccharides from glycoproteins and glycopeptides having N-linked carbohydrates. This action is in contrast to that of endoglycosidases, such as Endo F, Endo H, and Endo D, which neither release full length oligosaccharides nor cleave all common classes of N linked oligosaccharides from glycoproteins. PNGase F is a particularly useful PNGase because it shows particularly high activity toward most glycoproteins, and because it has a very broad substrate specificity. In contrast, the other well characterized PNGase, PNGase A, does not cleave sialylated oligosaccharides and exhibits lower activity toward glycoproteins.

By Endo F activity is meant an endo-$\beta$-N-acetyl glucosaminidase enzyme activity which cleaves carbohydrate moieties of a glycoprotein at a position not adjacent to an asparagine residue of the peptide; one such enzyme is isolated from *Flavobacterium meningosepticum*. Endo F acts on high mannose and biantennary type N linked oligosaccharides to release a shortened oligosaccharide.

In contrast to commercial preparations (N-glycanase TM, Genzyme, Boston, Mass.; and Glycopeptidase F, Boehringer Mannheim) and other preparations of PNGase F isolated from naturally-occurring cells as described above, the present invention provides PNGase free from contamination with Endo F, without substantial decrease in yield of PNGase F. The PNGase of the invention avoids Endo F interference in PNGase preparations and thus simplifies the detailed structural analysis of the oligosaccharides of glycopeptides or glycoproteins, and production of full length oligosaccharides from these glycopeptides or glycoproteins. In addition, Endo F contamination can result in a protein or peptide product having one or more single N-acetylglucosamine residues remaining on it, and may also result in a heterogenous mixture of such peptide products. Complete deglycosylation is desirable in peptide sequencing, and in studies of functions of the carbohydrates of glycoproteins.

By enzyme sample is meant a liquid sample having enzymatic activity, or a lyophilized powder which may be reconstituted to provide a solution having enzyme activity.

In preferred embodiments, the PNGase F activity is active on sialylated oligosaccharides and glycoproteins; and the PNGase F activity is identical to activity of *Flavobacterium meningosepticum* PNGase.

By sialylated glycoprotein is meant a protein having sialic acid groups, for example, serum glycoproteins including tPA, factor VIII, glucocerebrosidase and erythropoietin.

By glycoprotein and glycopeptide is meant any short or long amino acid sequence having N linked carbohydrate moieties. Endo F products of such glycoproteins differ from PNGase products in that they leave an N acetylglucosamine residue attached to the glycosylated asparagine residue.

In a related aspect, the invention features an enzyme sample having a PNGase activity identical or substantially identical (i.e., having similar enzymatic activity, and having a similar amino acid sequence with generally conservative amino acid differences) to an enzyme present in a bacterial species.

In preferred embodiments, the bacterial species is of the genus *Flavobacterium* or *Cytophaga*.

The enzymes of the invention can be used to produce a carbohydrate or protein or polypeptide sample which is completely free from Endo F products of the glycoprotein, or glycopeptide by treating a glycoprotein or glycopeptide with the enzyme. The full length oligosaccharides (i.e., those having an intact core) released from glycoproteins provide useful standards for glycoprotein analysis, and may be useful to allow targeting of proteins to macrophages, or have useful immunomodulatory activity. The pure samples also allow ready study of the biological activity of these carbohydrates. These carbohydrates can be used without need for HPLC purifications to remove Endo F products.

The enzymes of the invention can be used to completely deglycosylate an asparagine-glycoprotein or glycopeptide. This is useful for protein sequencing, isoelectric focusing, peptide mapping, and in the two dimensional electrophoresis of glycopeptides and glycoproteins.

Enzymes of the invention are preferably coded for by purified nucleic acid sequences preferably carried on a vector, for example, a plasmid, cosmid, or virus. By purified nucleic acid is meant a nucleic acid isolated from its natural environment, for example, a DNA sequence positioned adjacent to DNA sequences with which it does not naturally occur.

In preferred embodiments, the enzyme has an amino acid sequence having at least 40% homology with the amino acid sequence of a naturally-occurring bacterial enzyme having PNGase activity, e.g., a PNGase activity naturally existing in *Flavobacterium meningosepticum* or related *Flavobacterium* or *Cytophaga* species. More preferably the enzyme has 60% or even 90% homology with the natural amino acid sequence, especially at the amino acid sequences responsible for the PNGase activity of the enzyme. Less preferably, the PNGase coding sequences of the invention may have a nucleic acid sequence identical to that of a eucaryotic PNGase, e.g., almond. Homology is determined by techniques well known to those in the art, generally entailing lining u of amino acid sequences to maximize the homology observed.

In other preferred embodiments, the nucleic acid sequence has homology with the DNA sequence of a PNGase F gene present in pGB29, deposited in the ATCC and assigned the number 67987. By homology is meant the ability to hybridize specifically with any portion of the nucleic acid encoding the PNGase F gene present in pGB29. The nucleic acid sequence preferably is provided within a host cell which lacks Endo F activity and which is heterologous (i.e., of a different species from that from which the PNGase gene is isolated); examples are *Escherichia, Streptomyces,* and *Bacillus* species, e.g., *S. lividans*.

By specific hybridization is meant conditions in which any portion of the nucleic acid encoding PNGase F on pGB29 is able to hybridize to another DNA sequence to allow detection and isolation of any DNA sequence encoding a protein having PNGase activity in the presence of unrelated sequences, such as the genomic DNA of any organism, including other *F. meningosepticum* strains, and other *Flavobacterium* and *Cytophaga* strains which contain a PNGase gene.

More preferably, the nucleic acid sequence has sufficient homology with any portion of the DNA sequence of a PNGase F gene present in pGB29 to hybridize under stringent hybridization conditions with that gene. Such conditions are well known in the art. They depend upon the actual DNA sequence of the nucleic acid. For example, Hanahan et al., 100 Method. Enzymol. 333–342, 1983 describe specific probes as those able to hybridize, under the standard conditions they provide, at a hybridization temperature of 3 degrees below the sum of 2 degrees multiplied by the number of A-T base pairs plus 4 degrees multiplied by the number of G-C base pairs. For mixed nucleic acid sequences, or sequences longer than about 30 bases other well known standard formulae are available.

Most preferably, the nucleic acid sequences has at least 90% linear homology with the DNA sequence of a PNGase F gene in pGB29.

The invention allows production of a pure enzyme sample having high PNGase activity up to 10–100 or more fold greater than the activity obtainable from naturally-occurring sources. This sample lacks any Endo F activity.

Other features and advantages of the invention will be apparent from the following description of the preferred embodiments thereof, and from the claims.

BRIEF DESCRIPTION OF THE DRAWINGS

The drawings will first briefly be described.

DESCRIPTION OF THE PREFERRED EMBODIMENTS

PNGase F

Figure 1:
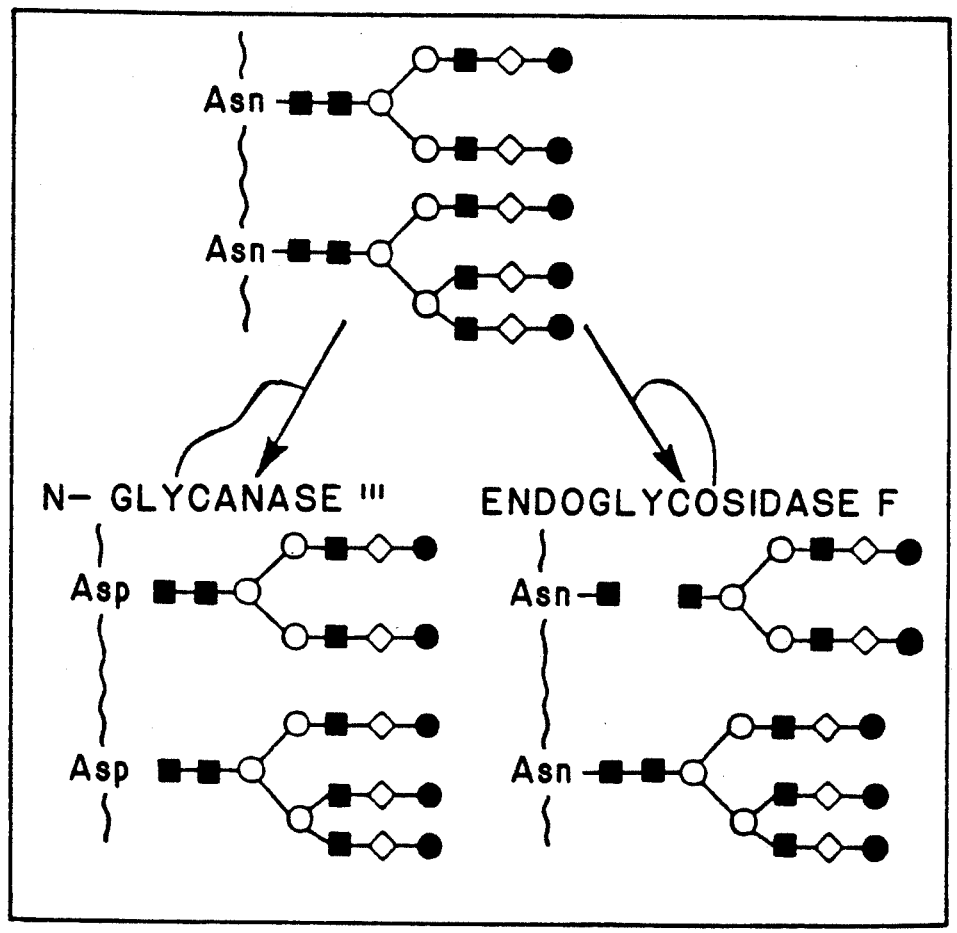
FIG. 1 is a diagrammatic representation of enzymes PNGase and Endo F (shown as Endoglycosidase F). The wavy lines represent a peptide or protein; Asn represents an asparagine residue; Asp represents an asparatic acid residue; filled-in square boxes represent an N-acetylglucosamine residue; open circles represent mannose; open diamonds represent galactose; and filled-in circles represent sialic acid.

One example of a protein having PNGase F activity is the enzyme produced by a *Flavobacterium meningosepticum* strain deposited as ATCC strain number 33958. There will now be described the identification and cloning of a PNGase F gene from *Flavobacterium meningosepticum*, and the use of that gene for the production of the PNGase F enzyme in a heterologous host. Included is a description of insertion of the Flavobacterium DNA into an *E. coli* vector, isolation of a clone containing a PNGase F gene, and expression of this DNA within *E. coli* cells.

A total *F. meningosepticum* (ATCC 33598) DNA clone bank was constructed as follows. *F. meningosepticum* ATCC 33958 cells were grown at 22° C. in M9 medium (Davis et al., Advanced Bacterial Genetics, Cold Spring Harbor Laboratory, Cold Spring Harbor, N.Y., p. 203, 1980) supplemented with 5 g/l Casamino acids (Difco). Total DNA was isolated using the method of Marmur, 3 J. Mol. Biol. 203, 1961, and partially cleaved with Sau3A restriction enzyme, using the method described by Maniatis et al. Molecular Cloning: A Laboratory Guide, Cold spring Harbor, 1987. DNA fragments in the 3–10 kb range were resolved by agarose gel electrophoresis, purified by electroelution, and ligated to BamHI cleaved, and alkaline phosphatase-treated, cloning vector pGB3. pGB3 was derived from pBSSK+, Stratagene, La Jolla, Calif. by replacing its SacI and ApaI sites with BglII sites. The resultant recombinant plasmids were used to transform *E. coli* SCS1 (Stratagene, La Jolla, Calif.). Twenty thousand primary clones were stored as duplicated colony banks on Optibind nitrocellulose membranes (Schleicher and Schuell, Keene, N.H.) at a density of 2–4 thousand per membrane, using the method described by Hanahan et al., 100 Meth. Enzymol. 333, 1983.

Oligonucleotide probes were designed to hybridize specifically to the N-terminal coding sequence of mature PNGase F, and thereby to be useful to identify the PNGase gene in the *E. coli* clone bank of *F. meningosepticum* DNA. The N-terminal amino acid sequence of PNGase F was determined on enzyme that had been purified by the method of Tarentino et al., 24 Biochem 4665, 1985 and subsequently eluted from a gel as a single band following PAGE. An oligonucleotide probe was designed to identify the corresponding coding region of the PNGase F gene by colony hybridization using methods described by Struhl, Current Protocols in Molecular Biology, John Wiley and Sons, 1987. This probe was a mixture of 20 base oligonucleotides representing all possible coding sequences for the region of the sequenced N-terminus of PNGase F which had the lowest corresponding codon degeneracy.

Clones carrying the PNGase F gene were identified by probing the colony bank with the labeled oligonucleotide mixture. Colonies on each of duplicate nitrocellulose membranes from the colony bank were lysed and their DNA bound to the membrane. The membranes containing the bound clone bank DNA were incubated in SSC buffer for 48 h at 40° C. with a $^{32}$P-labeled oligonucleotide mixture in order to allow hybridization. Non-specifically bound radioactive probe was washed off the filters at 48° C., and the washed filters exposed to X-ray film for 48 h. After development, hybridization signals were detected in the same positions on the autoradiograms of duplicate filters for 10 potential PNGase F clones. Bacteria were isolated from positions on master filters corresponding to those of the signals on the above autoradiograms. The isolates were plated on nitrocellulose membranes placed on the surface of the agar at lower colony densities (50–200 colonies/membrane), and screened again with probe. One clone identified in the above experiment contained a recombinant plasmid, named pGB29, which contains the PNGase F gene of *F. meningosepticum*. Southern hybridization experiments (68 Meth. Enzymol. 152, 1979), carried out as recommended by the supplier of Optibind membranes demonstrated that the major band hybridizing to the oligonucleotide probe for the PNGase F N-terminal coding sequence from HindIII and EcoRI digests of *F. meningosepticum* DNA also hybridized to pGB29 plasmid DNA isolated from this clone using the method of Birnboim, 100 Meth. Enzymol. 243, 1983.

Figure 2:
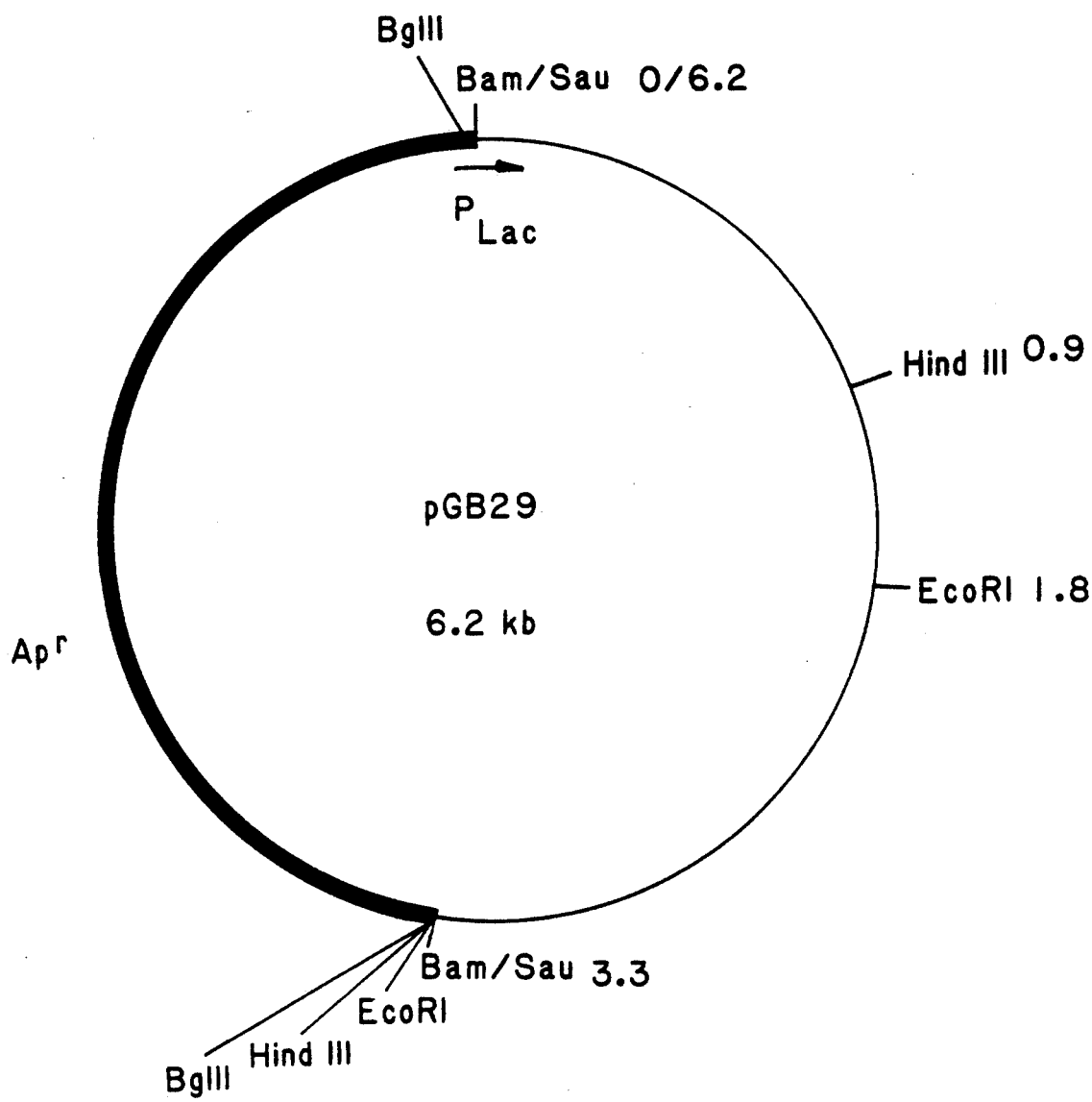
FIG. 2 is a diagrammatic representation of pGB29, formed from pGB3 vector DNA (shown by a thick black line) and *F. meningosepticum* genomic DNA (shown by a thin line). The location of various restriction enzyme sites is shown, in kilobases, with reference to the BamHl/SauIIIA hybrid site at position 0 kilobases. $P_{lac}$ represents the lac promoter, and $Ap^r$ represents a gene providing ampicillin resistance. (The positions of some EcoRI sites are not shown.)

A more rigorous demonstration that pGB29 carried the PNGase F gene was obtained when this plasmid was sequenced by the method of Sanger et al., 74 Proc. Nat. Acad. Sci. USA, 5463, 1977. The DNA sequence from pGB29 indicated that this plasmid carries the intact N-terminal coding region of the PNGase F gene. The predicted amino acid sequence over this region exactly matches that of the sequenced N terminus of purified PNGase F, indicating that this plasmid contains the PNGase gene of F. meningosepticum. The piece of *F. meningosepticum* DNA carried by pGB29 begins approximately 150 base pairs upstream of the first of two possible PNGase F start codons on the $P_{lac}$ promoter side of the pGB3 DNA, as shown in FIG. 2. Restriction analysis of pGB29 using BglII, EcoRI, and HindIII demonstrated that pGB29 carries approximately 3.3 kb of *F. meningosepticum* DNA, in addition to the 2.95 kb of pGB3 vector DNA. Sites for these restriction enzymes are indicated in FIG. 2.

Expression of Recombinant PNGase F

*E. coli* SCS1 cells containing pGB29 were grown in LB medium (10 g tryptone, 5 g yeast extract, and 10 g NaCl/liter, pH 7.5) at 37° C. with vigorous aeration, harvested by centrifugation, and resuspended in 1/10 volume of ice cold cracking buffer (50 mM Tris, pH 7.5, 1 mM PMSF, and 10 mM EDTA). Lysozyme was added to 1 mg/ml, and incubation continued on ice for 30 min to produce protoplasts. Protoplasts were broken by sonication, as described in Manual of Methods for General Bacteriology (American Society for Microbiology, 1981). The results of assays for PNGase F activity on the above cell extracts and culture supernatants from *E. coli* SCS1 alone, and containing pGB29, were performed using an UnLinkit-N ™ Glycanalysis ™ kit, as recommended by the supplier (Genzyme, Boston, Mass.). The control strain, without pGB29, had no detectable PNGase activity in either the cell extract or the culture supernatant. In contrast, the same strain containing pGB29 contained PNGase F activity, the majority of which was cell-associated.

Several aspects of production of PNGase F by fermentation of *E. coli* SCS1 containing pGB29 make this recombinant system preferable, compared to fermentation of *F. meningosepticum*. Assay for Endo F activity in extracts from *E. coli* SCS1 containing pGB29 demonstrated that these extracts did not contain detectable levels of Endo F. Endo F was assayed with $^3$H labeled high mannose oligosaccharides that were prepared by reducing PNGase F released oligosaccharides with NaB$^3$H$_4$. Oligosaccharides were released, isolated and labeled as described by Hirani et al., 162 Analytical Biochemistry 485, 1987. In this assay, cell extract was incubated with radiolabeled oligosaccharides in 0.2M sodium acetate, pH 5.5, for 1 h at 37° C. At the end of the incubation period concanavalin A-agarose was added to precipitate the oligosaccharide. The precipitate was harvested by centrifugation. Endo F activity was detected by release of radioactivity into the supernatant. The lack of contaminating Endo F activity eliminates interference by this enzyme in the release of full length oligosaccharides for structural analysis or oligosaccharide production. In addition, these extracts contained substantially more PNGase F activity than extracts from the same volume of *F. meningosepticum* fermentation. Elevated production of PNGase F, faster growth rate of *E. coli* SCS1 containing pGB29, compared to *F. meningosepticum*, and the lack of Endo F contamination make production of PNGase F in the recombinant system advantageous.

Purification of Recombinant PNGase F

A protocol for purification of PNGase F from *E. coli* SCS1/pGB29 cell extracts is as follows. In the first step, crude cell extracts were brought to 55% saturation with ammonium sulfate and stirred for 2 h. The protein precipitate, containing the bulk of the PNGase activity, was harvested by centrifugation and dissolved in a minimal volume of a solution containing: 50 mM Tris, pH 7.1, 0.7M ammonium sulfate, 5 mM EDTA, and 0.1M PMSF. For the second step, the preparation was loaded onto a phenyl superose HR 5/5 1 ml column (Pharmacia LKB Biotechnology, Inc., Piscataway, N.J.) and washed with a solution containing: 50 mM Tris, pH 7.1, 0.7 ammonium sulfate, 5 mM EDTA, and 0.1 mM PMSF. The bound PNGase F was eluted from the column using an ammonium sulfate gradient decreasing from 0.7–0M in a base solution containing: 50 mM Tris pH 7.1, 5 mM EDTA, and 0.1 mM PMSF. Fractions containing PNGase F were then dialysed to change the buffer to 10 mM sodium acetate, pH 5.5. As a third step, the sample was loaded on a Mono S HR 5/5 1 ml column (Pharmacia LKB Biotechnology, Inc. Piscataway, N.J.) equilibrated with a solution containing: 10 mM sodium acetate, pH 5.5, and 0.1 mM PMSF. PNGase F activity was eluted from the column using a sodium chloride gradient increasing from 0 0.5M in the same base solution. Fractions containing PNGase F activity were pooled and concentrated in an Amicon (Amicon Division, W. R. Grace & Co., Danvers, Mass.) ultrafiltration cell using a PM-10 membrane.

Utility

The recombinant PNGase F of the invention, free from Endo F contamination, is useful for cleavage of $\beta$-aspartylglycosylamine linkages of N-linked carbohydrate chains of glycoproteins to yield full length oligosaccharides suitable for structural analysis or for industrial or therapeutic use. It is also useful for provision of polypeptides free of carbohydrate moieties which can be used for peptide sequencing, peptide mapping, and as agents having enhanced therapeutic characteristics.

Deposit

An *E. coli* (SCS1) strain harboring the plasmid pGB29 was deposited on May 16, 1989, with the ATCC and assigned the number 67987.

Applicants' assignee, Genzyme Corporation, acknowledges its responsibility to replace this culture should it die before the end of the term of a patent issued hereon, 5 years after the last request for a culture, or 30 years, whichever is the longer, and its responsibility to notify the depository of the issuance of such a patent, at which time the deposit will be make irrevocably available to the public. Until that time the deposit will be made available to the Commissioner of Patents under the terms of 37 CFR 1.14 and 35 USC 122.

Other embodiments are within the following claims. The above examples are not limiting to the present invention, and those skilled in the art will recognize that isolation of equivalent nucleic acids encoding equivalent PNGases can be achieved by following the described example, or by use of the gene, deposited with the ATCC, encoding for PNGase F as a hybridization probe. As described above, this invention is meant to include any gene encoding for PNGase activity, and particularly for any gene which has substantial homology to DNA encoding PNGase F, and therefore is able to hybridize under stringent conditions to segments of DNA from that gene.

We claim:

1. A purified nucleic acid comprising a nucleotide sequence encoding an enzyme having PNGase activity produced by the bacteria *Flavobacterium meningosepticum*.

2. The purified nucleic acid of claim 1 wherein said nucleic acid is provided within a host of cell lacking Endo F activity, said host cell being of the genus *Escherichia*.

3. The purified nucleic acid of claim 2, wherein said host cell is *E. coli*.

4. A method for producing an enzyme substantially identical to PNGase F and being completely free of Endo F activity, comprising the steps of:
   a) providing an nucleic acid comprising a nucleotide sequence encoding an enzyme substantially identical to PNGase F,
   b) introducing said nucleic acid into a host cell lacking Endo F activity to provide a recombinant cell, said host cell being of the genus *Escherichia*,
   c) culturing said recombinant cell under conditions which permit expression of said enzyme, and
   d) recovering said enzyme.

5. The method of claim 4 wherein said host cell is *E. coli*.

6. The nucleic acid of claim 1, wherein said nucleic acid sequence has at least 90% homology with the PNGase F gene present in pGB29, deposited in the ATCC and assigned the number 67987.

7. the nucleic acid of claim 1 wherein said nucleic acid sequence is able to hybridize under stringent conditions with a 30 base pair sequence of the PNGase F gene present in pGB29, deposited in the ATCC and assigned the number 67987.

8. The purified nucleic acid of claim 1 wherein said nucleic acid sequence is carried on a plasmid.

9. An isolated and purified nucleic acid able to specifically hybridize under stringent conditions with a 20 base pair sequence of the PNGase F gene present in pGB29, deposited in the ATCC and assigned the number 67987.

10. A purified enzyme comprising peptide-$N^4$-(N-acetyl-beta-N-glucosaminyl) asparagine aminidase, said enzyme being further capable of cleaving sialylated oligosaccharides and being completely free of endo-beta-N-acetylglucosaminidase F, said enzyme being substantially identical to *Flavobacterium meningosepticum* PNGase.

* * * * *